(12) United States Patent
Allen, Jr. et al.

(10) Patent No.: US 10,143,816 B2
(45) Date of Patent: Dec. 4, 2018

(54) MEDICAL BITE BLOCK AND METHOD

(71) Applicants: Barnhardt Manufacturing Company, Charlotte, NC (US); Sanada LLC, Bismarck, NC (US)

(72) Inventors: Hiram Charles Allen, Jr., Indian Trail, NC (US); Diana J. Roloff, Bismarck, ND (US)

(73) Assignee: Barnhardt Manufacturing Company, Charlotte, NC (US)

( * ) Notice: Subject to any disclaimer, the term of this patent is extended or adjusted under 35 U.S.C. 154(b) by 102 days.

(21) Appl. No.: 15/377,253

(22) Filed: Dec. 13, 2016

(65) Prior Publication Data

US 2018/0161534 A1    Jun. 14, 2018

(51) Int. Cl.
| | |
|---|---|
| *A61M 16/04* | (2006.01) |
| *B29C 47/00* | (2006.01) |
| *B29C 53/56* | (2006.01) |
| *B29K 1/00* | (2006.01) |
| *B29L 31/00* | (2006.01) |
| *A61B 90/16* | (2016.01) |

(52) U.S. Cl.
CPC ..... *A61M 16/0493* (2014.02); *B29C 47/0016* (2013.01); *B29C 47/0066* (2013.01); *B29C 53/56* (2013.01); *A61B 90/16* (2016.02); *A61M 2207/00* (2013.01); *B29K 2001/12* (2013.01); *B29L 2031/753* (2013.01)

(58) Field of Classification Search
CPC ............. A61F 13/2051; A61F 13/2031; A61F 13/2008; A61F 13/2071; A61F 13/2022; A61F 13/551; A61F 13/2068; A61M 16/0493; A61B 90/16; A61B 6/14
See application file for complete search history.

(56) References Cited

U.S. PATENT DOCUMENTS

| | | |
|---|---|---|
| 1,812,655 A | 6/1931 | Ladd |
| 1,985,667 A | 12/1934 | Nelson et al. |
| 4,233,025 A | 11/1980 | Larson et al. |
| 4,705,514 A | 11/1987 | Barnard |
| 2010/0236548 A1 | 9/2010 | Reis et al. |

OTHER PUBLICATIONS

Wrapped Rolls | Richmond Dental | http://www.richmonddental.net/products/wrapped-rolls/?ind=dental&category=disposables, dated Nov. 15, 2016, 2 pages.
International Search Report for PCT/US2016/066340 dated Feb. 24, 2017.

*Primary Examiner* — Ellen C Hammond
(74) *Attorney, Agent, or Firm* — Shumaker, Loop & Kendrick, LLP

(57) ABSTRACT

A bite block for use in a mouth of a patient to hold the mouth in a spaced-apart position that includes a condensed fiber block having a predetermined length suitable for being inserted into the mouth of the patient and positioned between upper and lower molars and a wrapper yarn repeatedly wrapped around the block along its length. An adhesive strand in the wrapper yarn is positioned on an outer surface of the fiber to maintain the block in its condensed state.

7 Claims, 3 Drawing Sheets

MEDICAL BITE BLOCK AND METHOD

TECHNICAL FIELD AND BACKGROUND OF THE INVENTION

This invention relates to a patient airway bite block of the general type used together with laryngeal mask airways (LMAs), oral endotracheal tubes (ETTs) and similar patient airways. A patient under general anesthesia must have the airway maintained in an open position in order to assure adequate ventilation. This is most often accomplished by intubating the patient using an LMA or an ETT. The LMA can serve in place of either a patient facemask or an endotracheal tube and constructed with a distal portion, which is a cuffed disc, which fits around the patient's larynx in the posterior hypopharynx and a more proximal element, which is analogous to an endotracheal tube. LMAs are placed in anesthetized patients blindly and the exiting tube portion is positioned directly in the mid-line of the mouth.

Use of an LMA or an ETT in an anesthetized patient, requires a protocol that assures that the patient's airway remains open and thus requires that certain events be avoided. First, the patient may bite down on the airway tube and cause airway obstruction. This can lead very quickly to hypoxemia (i.e., dangerously low levels of oxygen in the blood). Second, biting by the patient's incisors can cause actual severing of the LMA or ETT and subsequent loss of control of the airway. Third, secretions tend to accumulate in the back of the throat during general anesthesia because there is a loss of the normal swallowing reflex in the anesthetized patient. In a lightly anesthetized patient or in a patient that is awakening from general anesthesia, such secretions can cause laryngospasm and subsequent airway closure. Therefore, it is best to keep the teeth apart with the soft bite block to allow these secretions to be suctioned from the mouth. Because of the above-described problems encountered using an LMA or an ETT, a bite block placed between the teeth of the anesthetized patient is necessary.

Conventional oral airways, which are usually used in patients anesthetized with their airway secured with oral endotracheal tubes, are not suitable for use with LMAs because such devices seat themselves directly in the mid-line of the mouth and thus, compete for the space where the tube portion of the LMA exits in the mouth. In addition, the posterior portion of the oral airway, which is used to hold the tongue forward when used with an endotracheal tube, impinges on the cuffed portion of the LMA in the hypopharynx resulting in the cuff not functioning properly. Among the solutions, practitioners have employed to provide bite blocks for patients with LMAs include the modification of other products, which are intended for completely different uses. For example, a bite guard for use with gastroscopy patients has been described for use as a bite block. This device is not suitable for use with an LMA because (1) it is not designed for use with LMAs and is not sized appropriately, (2) it seats in the center of the mouth and (3) it is not safe for patients with frontal dental bridgework since this is the area that will bite down on the device.

SUMMARY OF THE INVENTION

It is therefore an object of the present invention to provide a bite block that can be used with LMAs, ETTs and similar airway devices.

It is another object of the invention to provide a bite block that does not interfere with other oral appliances attendant to use of general anesthesia during a medical procedure.

It is another object of the invention to provide a bite block that can be held in the side of the mouth between the molars during use of an LMA or an ETT.

These and other objects and advantages of the invention are achieved by providing a bite block for use in a mouth of a patient to hold the mouth in a spaced-apart position that includes a condensed fiber block having a predetermined length suitable for being inserted into the mouth of the patient and positioned between upper and lower molars and a wrapper yarn repeatedly wrapped around the block along its length. An adhesive is positioned on an outer surface of the fiber to maintain the block in its condensed state. The bite block according to one preferred embodiment has a density of 0.23 $g/cm^3$ and a resistance to compression sufficient to maintain a thickness of at least 7 mm under an applied pressure of 7 $kg/cm^2$.

According to another embodiment of the invention, the wrapper yarn has at least two plies and one of the two plies is an adhesive adapted to be dissolved onto an outer surface of the sliver.

According to another embodiment of the invention, the adhesive strand comprises cellulose acetate.

According to another embodiment of the invention, the fiber block comprises cotton sliver.

According to another embodiment of the invention, a bite block for use in a mouth of a patient to the mouth in a spaced-apart position is provided, that includes a condensed, cylindrical cotton sliver block having a predetermined length suitable for being inserted into the mouth of the patient between upper and lower molars. A yarn is repeatedly wrapped around the block along its length and an adhesive is positioned on an outer surface of the block and adapted to be dissolved onto an outer surface of the block to maintain the block in its condensed state. The wrapper yarn has two yarn plies and one of the two plies of the yarn is an adhesive.

According to another embodiment of the invention, the adhesive is cellulose acetate.

According to another embodiment of the invention, a method is provided for forming a bite block for use in a mouth of a patient to hold the mouth open in a spaced-apart position and includes the steps of forming a sliver and condensing the sliver into a sliver block. A yarn is wrapped repeatedly around the condensed sliver block along its length and an adhesive strand is applied onto an outer surface of the sliver block to maintain the sliver in its condensed state. The sliver is cut into a predetermined length suitable for being inserted into the mouth of the patient between upper and lower molars.

According to another embodiment of the invention, the step of condensing the sliver into a sliver block includes the step of passing an uncondensed sliver through an orifice that narrows in a downstream direction sufficiently to condense the sliver into a desired dimension perpendicular to the downstream direction of travel of the sliver.

According to another embodiment of the invention, the orifice is circular in cross-section and condenses the sliver into a cylinder having a desired diameter.

According to another embodiment of the invention, the step of wrapping the yarn includes the step of providing a yarn having at least two plies, wherein at least one of the plies is an adhesive in the form of a strand.

According to another embodiment of the invention, the method includes the step of dissolving the adhesive strand onto an outer surface of the block along its length.

According to another embodiment of the invention, the step of forming the sliver includes the step of forming the sliver from cotton staple fibers or any other natural of synthetic staple fibers.

According to another embodiment of the invention, at least one of the yarn plies is a non-dissolving synthetic strand.

According to another embodiment of the invention, the bite block is between 16-20 mm in diameter and between 8-12 cm in length.

According to another embodiment of the invention, the step of forming the sliver block comprises the step of passing a plurality of uncondensed slivers simultaneously through an orifice that narrows in a downstream direction sufficiently to condense the sliver into a desired dimension perpendicular to the downstream direction of travel of the sliver.

According to another embodiment of the invention, the method includes the steps of condensing a sliver into a sliver block having a nominal diameter of 8-12 mm, wherein under a compression load of 7 kg/cm$^2$ the diameter of the sliver block is at least 7 mm.

According to another embodiment of the invention, the method includes the step of packaging a plurality of bite blocks for storage until use.

According to another embodiment of the invention, a method of forming a bite block for use in a mouth of a patient to hold the mouth in a spaced-apart position is provided and includes comprising the steps of forming a plurality of cotton slivers and condensing the slivers into a sliver block by passing a plurality of slivers simultaneously through an orifice that narrows in a downstream direction sufficiently to condense the sliver into a desired dimension perpendicular to the downstream direction of travel of the sliver, A yarn having at least two plies is wrapped repeatedly around the condensed sliver block along its length, wherein at least one of the plies is an adhesive in the form of a strand. The adhesive strand is dissolved onto an outer surface of the sliver block along its length to maintain the sliver in its condensed state and the sliver block is cut into a predetermined length to form a bite block suitable for being inserted into the mouth of the patient between upper and lower molars. The bite block is packaged for storage until use. The sliver block has a nominal uncompressed diameter of 8-10 mm, and under a compression load of 7 kg/cm$^2$ the diameter of the bit block is at least 7 mm.

According to another embodiment of the invention, the adhesive strand is cellulose acetate, and the step of dissolving the adhesive includes the step of passing the sliver block through an acetone bath.

BRIEF DESCRIPTION OF THE DRAWING FIGURES

The present invention is best understood when the following detailed description of the invention is read with reference to the accompanying drawings, in which.

DETAILED DESCRIPTION OF THE PREFERRED EMBODIMENT

Figure 1:
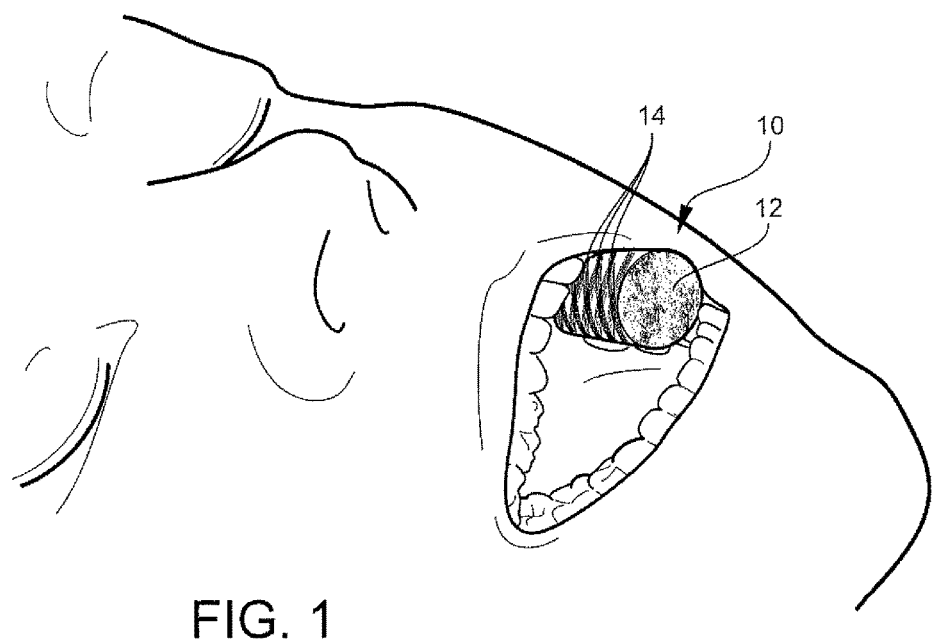
FIG. 1 is an environmental view showing a bite block according to an embodiment of the invention positioned between upper and lower molars of a patient before insertion of an airway.

Referring now to the drawings, a bite block according to a preferred embodiment of the invention is shown at reference numeral 10. The bite block 10 is formed of a tightly condensed bundle of fibers forming a fiber block 12 that is wrapped in the tightly condensed state with a wrapper yarn 14 applied, for example, by a braiding machine. A preferred sliver block 12 comprises staple cotton processed under medical grade cleanliness standards applicable to other medical products containing cotton. Other staple fibers can also be used, but staple cotton fiber has been found to be a preferred, suitable material. The wrapper yarn 14 preferably comprises a two-ply yarn wherein one ply is a synthetic filament yarn such as nylon, polyester, polyethylene, polypropylene or other suitable material, with nylon being the preferred filament yarn. The second ply is preferably a cellulose acetate yarn.

Figure 2:
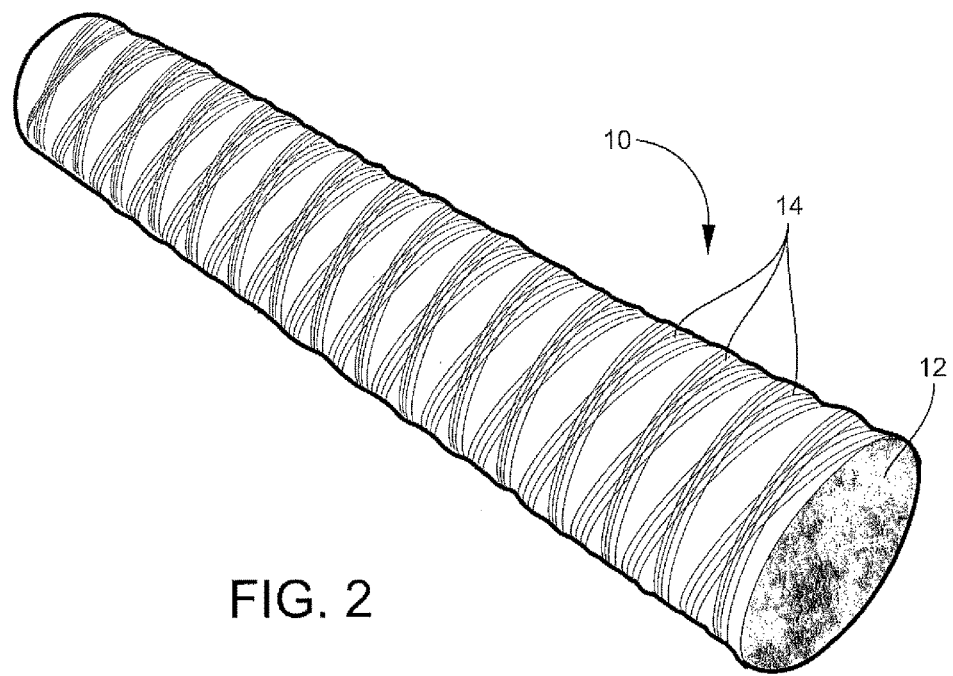
FIG. 2 is a perspective view of a bite block according to an embodiment of the invention.

As is shown in FIGS. 1 and 2, the wrapper yarn 14 is wrapped on the braiding machine in a crisscross pattern around the cylindrical sliver block 12 and prevents the condensed sliver block 12 from blooming, as described in further detail below.

Figure 3:
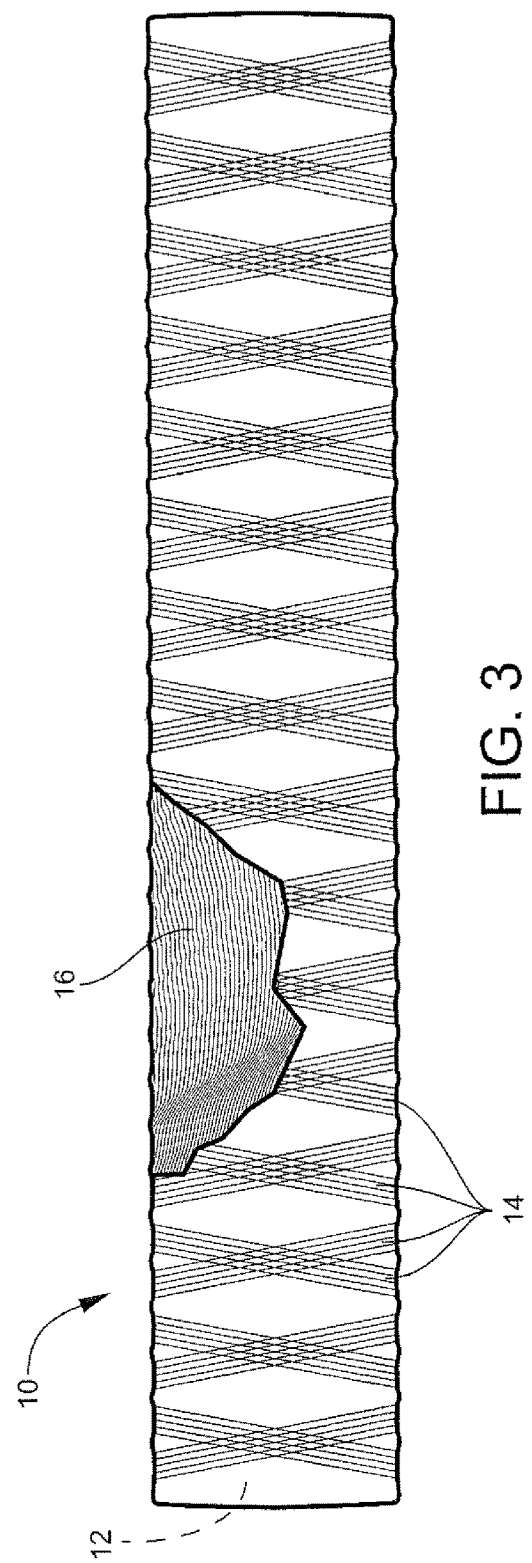
FIG. 3 is a side elevation of the bite block of FIGS. 1 and 2 with a section of wrapper yarn removed to show a covering layer of adhesive overlying the sliver block.

Referring to FIG. 3, the cellulose acetate yarn ply is dissolved during the manufacturing process described below and diffuses onto the surface of the sliver block 12. The diffused cellulose acetate acts as an adhesive 16 that further prevents blooming of the sliver block 12 and thus maintains the required compression of the bite block 10. A preferred nominal diameter for the bite block 10 as manufactured is about 20 mm.

Figure 4:
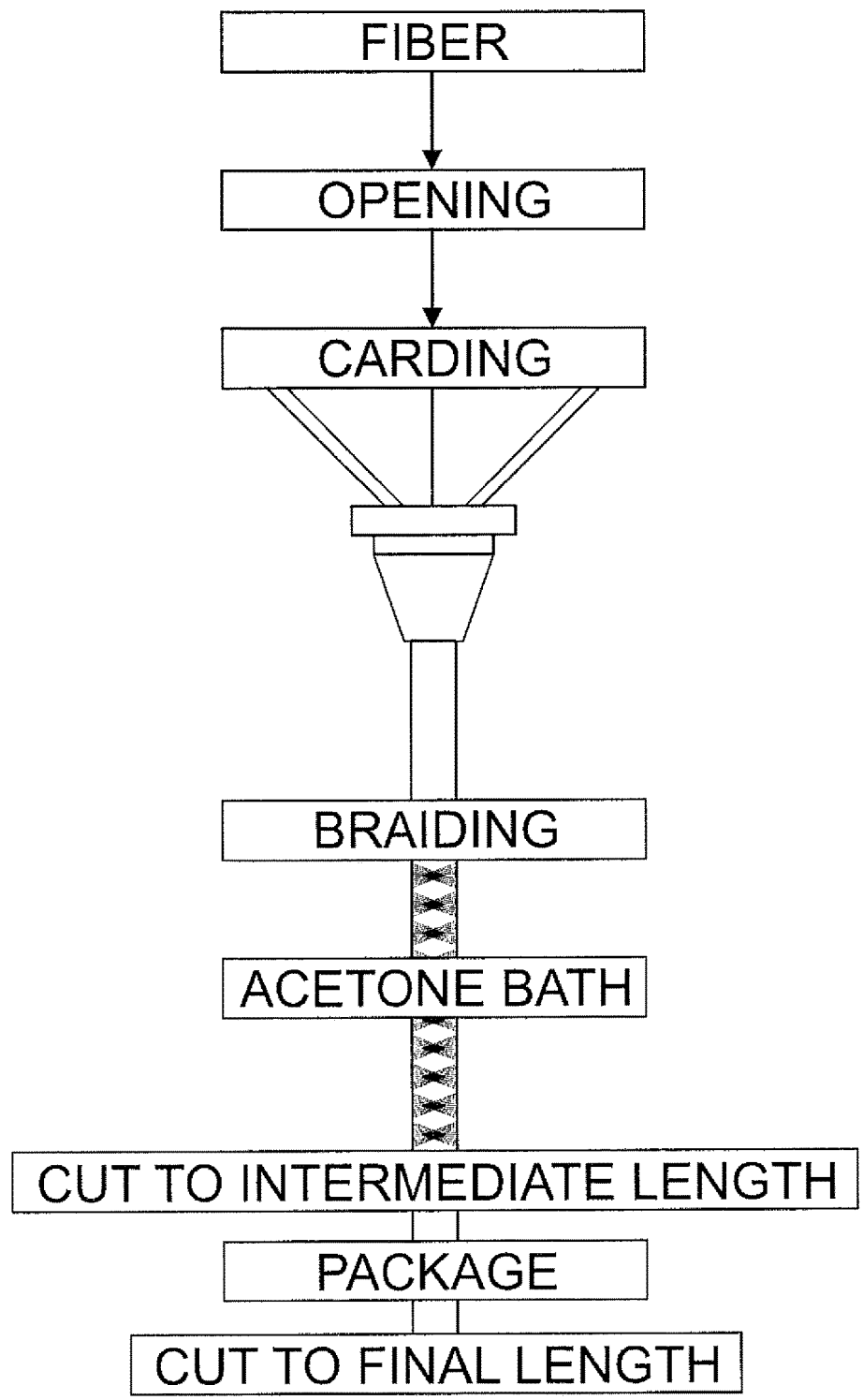
FIG. 4 is a flow diagram illustrating a preferred process for manufacturing the bite block according to the disclosure of this application.

FIG. 4 illustrates a preferred manufacturing process for the bite block 10. Fiber, such as cotton staple fiber, is opened and then carded by conventional textile processing equipment. The output of the cards is a sliver—a rope of parallel fibers with sufficient twist applied to hold the sliver block 12 together during subsequent processing. As shown, several slivers, for example, three slivers are formed into a single, tightly condensed sliver block 12 by simultaneously passing the slivers through a "trumpet", i.e., a funnel-shaped device with a downstream-narrowing orifice. Thus, for example, three 333-gram slivers are condensed into a single 1000-gram sliver block 12. Immediately at the downstream opening of the trumpet, the joined, condensed slivers are wrapped with the wrapper yarn 14 in a braiding machine, which may be any one of several types of braiding machines, such as a maypole braider.

In the preferred embodiment disclosed, the wrapped sliver block 12 is then conveyed to and through a bath of acetone in which the cellulose acetate yarn ply is dissolved into a thin film that coats the surface of the sliver block 12 and provides further resistance to the natural tendency of a compressed cotton fiber to bloom. The acetone has a very low vapor pressure and rapidly evaporates, leaving the sliver block 12 with both a wrapper yarn 14 of the remaining nylon component and an extremely thin adhesive coating 16.

Upon exiting the acetone bath, the continuous length of sliver block 12 is cut to an intermediate length, for example, 10 cm. These individual cut lengths of sliver blocks 12 may be packaged individually or bundled into groups of, for example, ten and packaged in a tube sufficiently large enough to accommodate the group and wrapped in a tubular paper package. The intermediate length sliver blocks 12 are then cut to a final length, for example, 100 mm and are then ready for consolidation into cartons for shipping.

The resulting bite block 10, according to one preferred embodiment, has a density of 0.23 g/cm$^3$ and a resistance to compression sufficient to maintain a thickness of at least 7 mm under an applied pressure of 7 kg/cm$^2$. The 7 mm minimum thickness under this degree of applied pressure is required because 7 mm is a standard diameter of an adult airway tube, and the force applied by a patient biting the bite block 10 should not restrict the airway.

A bite block according to the invention has been described with reference to specific embodiments and examples. Various details of the invention maybe changed without departing from the scope of the invention. Furthermore, the foregoing description of the preferred embodiments of the invention and best mode for practicing the invention are provided for the purpose of illustration only and not for the purpose of limitation, the invention being defined by the claims.

We claim:

1. A bite block for use in a mouth of a patient to hold the mouth in a spaced-apart position, comprising:
   (a) a condensed fiber block having a predetermined length suitable for being inserted into the mouth of the patient and positioned between upper and lower molars;
   (b) a wrapper yarn repeatedly wrapped around the block along its length;
   (c) an adhesive positioned on an outer surface of the fiber to maintain the block in its condensed state; and
   (d) wherein the block has a density of 0.23 g/cm$^3$ and a resistance to compression sufficient to maintain a thickness of at least 7 mm under an applied pressure of 7 kg/cm$^2$.

2. A bite block according to claim 1, wherein the wrapper yarn has at least two plies and one of the two plies comprises the adhesive.

3. A bite block according to claim 1, wherein the wrapper yarn has at least two plies and one of the plies comprises the adhesive, wherein the adhesive is a strand adapted to be dissolved onto an outer surface of the block.

4. A bite block according to claim 3, wherein the adhesive strand comprises cellulose acetate.

5. A bite block according to claim 1, wherein the fiber block comprises cotton sliver.

6. A bite block for use in a mouth of a patient to hold the mouth in a spaced-apart position, comprising:
   (a) a condensed cylindrical cotton sliver block having a predetermined length suitable for being inserted into the mouth of the patient between upper and lower molars;
   (b) a yarn repeatedly wrapped around the block along its length; and
   (c) an adhesive positioned on an outer surface of the block and adapted to be dissolved onto an outer surface of the block to maintain the block in its condensed state, wherein the wrapper yarn comprises two yarn plies and one of the two plies of the yarn comprises the adhesive.

7. A bite block according to claim 6, wherein the adhesive comprises cellulose acetate.

* * * * *